United States Patent [19]

Butler et al.

[11] Patent Number: 6,090,991
[45] Date of Patent: Jul. 18, 2000

[54] GAS PHASE ALKYLATION METHOD AND CATALYST

[75] Inventors: James R. Butler; Ashim Kumar Ghosh, both of Houston, Tex.

[73] Assignee: Fina Technology, Inc., Dallas, Tex.

[21] Appl. No.: 09/259,747

[22] Filed: Feb. 27, 1999

[51] Int. Cl.[7] .................................. C07C 2/68; C07C 2/64
[52] U.S. Cl. ............................................ 585/467; 585/449
[58] Field of Search ....................................... 585/467, 444

[56] References Cited

U.S. PATENT DOCUMENTS

| | | | |
|---|---|---|---|
| 4,107,224 | 8/1978 | Dwyer | 260/671 R |
| 4,169,111 | 9/1979 | Wight | 585/323 |
| 4,185,040 | 1/1980 | Ward et al. | 585/467 |
| 4,489,214 | 12/1984 | Butler et al. | 585/467 |
| 4,520,220 | 5/1985 | Watson et al. | 585/467 |
| 4,772,456 | 9/1988 | DeClippeleir et al. | 423/328 |
| 4,774,377 | 9/1988 | Barger et al. | 585/323 |
| 4,781,906 | 11/1988 | Cahen et al. | 423/328 |
| 4,922,053 | 5/1990 | Waguespack et al. | 585/449 |
| 5,358,698 | 10/1994 | Butler et al. | 422/218 |
| 5,847,255 | 12/1998 | Ghosh et al. | 585/467 |

*Primary Examiner*—Marian C. Knode
*Assistant Examiner*—Thuan D. Dang
*Attorney, Agent, or Firm*—John K. Abokhair; M. Norwood Cheairs

[57] ABSTRACT

Ethylbenzene is produced by alkylation over monoclinic silicalite catalysts having a weak acid site concentration of less than 50 micromoles per gram. A feedstock containing benzene and ethylene is applied to an alkylation reaction zone having at least one catalyst bed containing a monoclinic silicalite catalyst having a weak acid site concentration of less than 50 micromoles per gram. The alkylation reaction zone is operated at temperature and pressure conditions in which the benzene is in a gaseous phase to cause gas-phase alkylation of the aromatic substrate in the presence of the silicalite catalysts to produce an alkylation product. The alkylation product is then withdrawn from the reaction zone for separation and recovery.

13 Claims, 3 Drawing Sheets

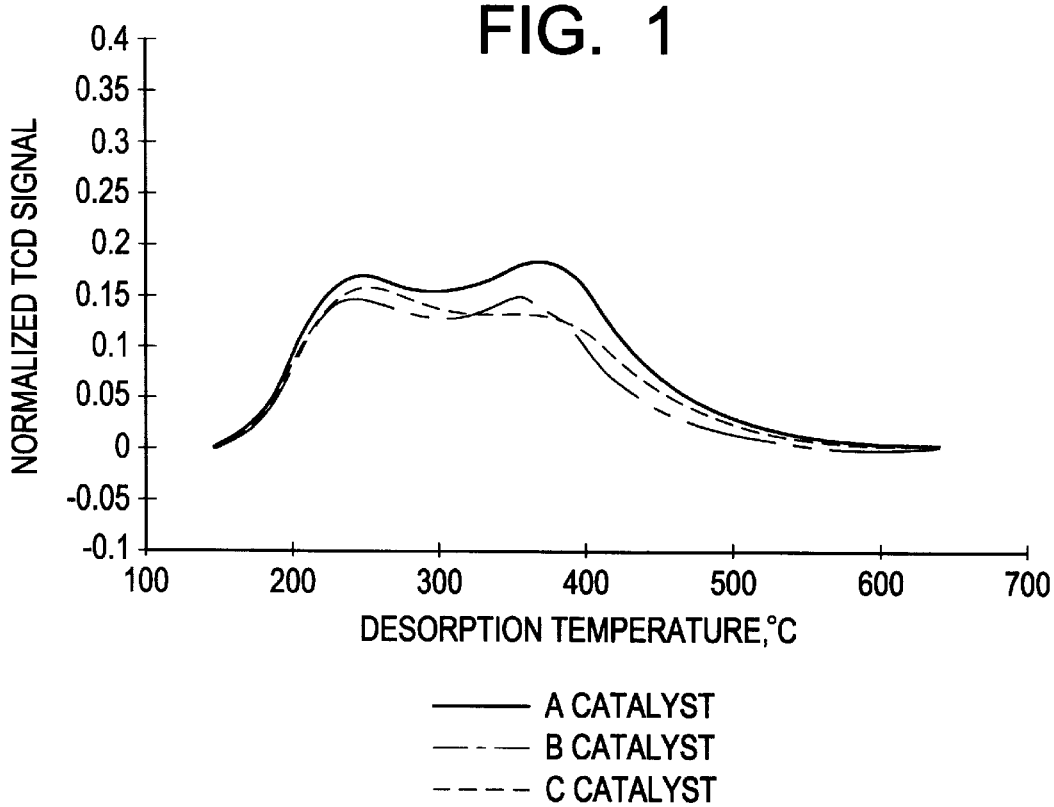
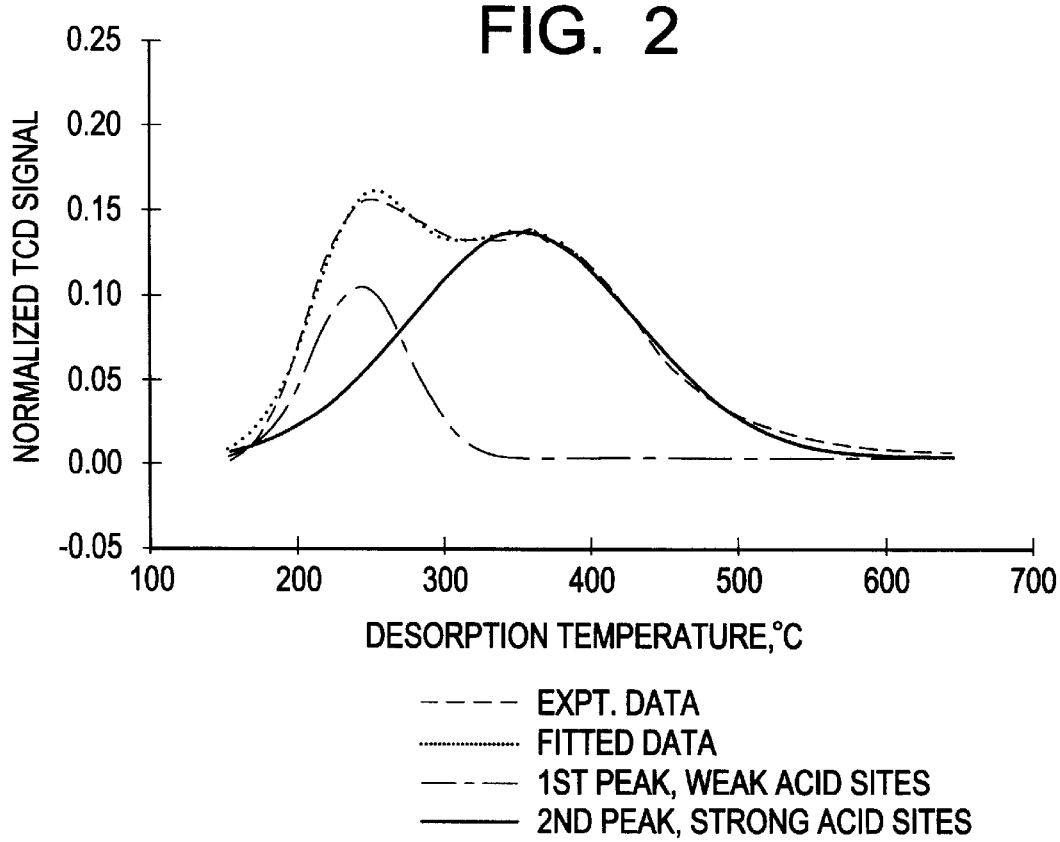

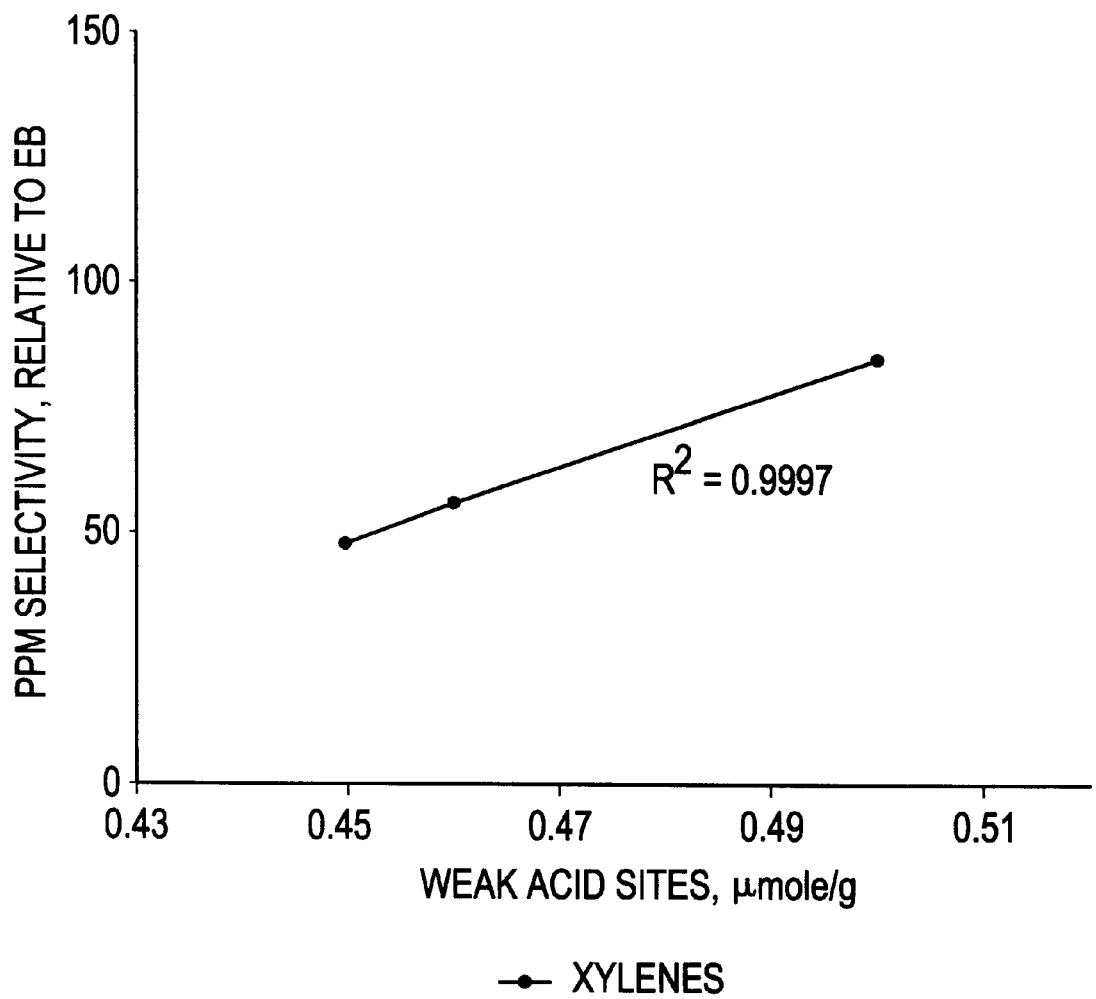

GAS PHASE ALKYLATION METHOD AND CATALYST

BACKGROUND

This invention relates to an aromatic alkylation process and catalyst involving vapor phase alkylation of an aromatic substrate over an improved silicalite aromatic alkylation catalyst. The improved catalyst and method provide alkylation products with decreased impurities and undesirable side reaction products.

Aromatic conversion processes which are carried out over molecular sieve catalysts are well known in the chemical processing industry. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and poly-alkyl benzenes may be coupled through various separation stages to a downstream transalkylation reactor. Such alkylation and transalkylation conversion processes can be carried out in the liquid phase, in the vapor phase or under conditions in which both liquid and vapor phases are present.

In efforts to improve commercial alkylation operations, emphasis is placed not only on the conversion efficiency of the catalyst but also on the byproducts that are generated. For example, in the manufacture of ethylbenzene, ethylene and benzene are introduced into an alkylation reactor in the presence of various catalysts. Some of the measured byproducts include diethylbenzene, xylene, propylbenzene, cumene, butylbenzene and other components referred to collectively as heavies. These byproducts have a negative effect on the purification of the desired product. Additionally, even when separated, these byproducts have to be removed from the system. Proper disposal adds to the cost of the intended product.

An example of vapor phase alkylation is found in U.S. Pat. No. 4,107,224 to Dwyer. Here, vapor phase ethylation of benzene over a zeolite catalyst is accomplished in a down flow reactor having four series-connected catalyst beds. The output from the reactor is passed to a separation system in which ethylbenzene product is recovered, with the recycle of polyethylbenzenes to the alkylation reactor where they undergo transalkylation reactions with benzene. The Dwyer catalysts include ZSM-5, ZSM-11, ZSM-12, ZSM-35, ZSM-38, and similar materials.

The molecular sieve silicalite is a well-known alkylation catalyst. For example, U.S. Pat. No. 4,520,220 to Watson et al. discloses the use of silicalite catalysts having an average crystal size of less than 8 microns and a silica/alumina ratio of at least about 200 in the ethylation of an aromatic substrate such as benzene or toluene to produce ethylbenzene or ethyltoluene, respectively. As disclosed in Watson et al., the alkylation procedure can be carried out in a multi-bed alkylation reactor at temperatures ranging from about 350°–475° C., with or without a steam co-feed. The reactor conditions in Watson et al. are such as to provide generally for vapor phase alkylation conditions.

Another procedure employing silicalite and involving the ethylation of benzene under vapor phase reaction conditions coupled with the recycle of polyethylbenzene containing products back to the alkylation reactor is disclosed in U.S. Pat. No. 4,922,053 to Waguespack. Here, alkylation is carried out at temperatures generally in the range of 370° C. to about 470° C. and pressures ranging from atmospheric up to about 25 atmospheres over a catalyst such as silicalite or ZSM-5. The catalysts are described as being moisture sensitive and care is taken to prevent the presence of moisture in the reaction zone. The alkylation/transalkylation reactor comprises four series-connected catalyst beds. Benzene and ethylene are introduced into the top of the reactor to the first catalyst bed coupled by recycle of a polyethylbenzene fraction to the top of the first catalyst bed as well as the interstage injection of polyethylbenzene and benzene at different points in the reactor.

Another process involving the use of a silicalite as an alkylation catalyst involves the alkylation of an alkylbenzene substrate in order to produce dialkylbenzene of a suppressed ortho isomer content. Thus, as disclosed in U.S. Pat. No. 4,489,214 to Butler et al., silicalite is employed as a catalyst in the alkylation of a monoalkylated substrate, toluene or ethylbenzene, in order to produce the corresponding dialkylbenzene, such as ethyl toluene or diethylbenzene. Specifically disclosed in Butler et al. is the ethylation of toluene to produce ethyltoluene under vapor phase conditions at temperatures ranging from 350°–500° C. As disclosed in Butler, the presence of ortho ethyltoluene in the reaction product is substantially less than the thermodynamic equilibrium amount at the vapor phase reaction conditions employed.

U.S. Pat. No. 4,185,040 to Ward et al. discloses an alkylation process employing a molecular sieve catalyst of low sodium content which is said to be especially useful in the production of ethylbenzene from benzene and ethylene and cumene from benzene and propylene. The $Na_2O$ content of the zeolite should be less than 0.5 wt. %. Examples of suitable zeolites include molecular sieves of the X, Y, L, B, ZSM-5, and omega crystal types, with steam stabilized hydrogen Y zeolite being preferred. Specifically disclosed is a steam stabilized ammonium Y zeolite containing about 0.2% $Na_2O$. Various catalyst shapes are disclosed in the Ward et al. patent. While cylindrical extrudates maybe employed, a particularly preferred catalyst shape is a so-called "trilobal" shape which is configured as something in the nature of a three leaf clover. The surface area/volume ratio of the extrudate should be within the range of 85–160 in.$^{-1}$. The alkylation process may be carried out with either upward or downward flow, the latter being preferred, and preferably under temperature and pressure conditions so that at least some liquid phase is present, at least until substantially all of the olefin alkylating agent is consumed. Ward et al. states that rapid catalyst deactivation occurs under most alkylating conditions when no liquid phase is present.

U.S. Pat. No. 4,169,111 to Wight discloses an alkylation/transalkylation process for the manufacture of ethylbenzene employing crystalline aluminosilicates in the alkylation and transalkylation reactors. The catalysts in the alkylation and transalkylation reactors may be the same or different and include low sodium zeolites having silica/alumina mole ratios between 2 and 80, preferably between 4–12. Exemplary zeolites include molecular sieves of the X, Y, L, B, ZSM-5, and omega crystal types with steam stabilized Y zeolite containing about 0.2% $Na_2O$ being preferred. The alkylation reactor is operated in a downflow mode and under temperature and pressure conditions in which some liquid phase is present. The output from the alkylating reactor is cooled in a heat exchanger and supplied to a benzene separation column from which benzene is recovered overhead and recycled to the alkylation reactor. The initial higher boiling bottoms fraction from the benzene column comprising ethylbenzene and polyethlybenzene is supplied to an initial ethylbenzene column from which the ethylbenzene is recovered as the process product. The bottoms product from the ethylbenzene column is supplied to a third column which is operated to provide a substantially pure diethylbenzene overheads fraction which contains from 10 to 90%, preferably 20 to 60% of diethylbenzene. The diethylbenzene overheads fraction is recycled to the alkylation reactor while a side cut containing the remaining diethylbenzene and triethylbenzene and higher molecular weight compounds is supplied to the reactor along with benzene. The effluent from the reactor is recycled through the heat exchanger to the benzene column.

U.S. Pat. No. 4,774,377 to Barger et al. discloses an alkylation/transalkylation process which involves the use of separate alkylation and transalkylation reaction zones, with recycle of the transalkylated product to an intermediate separation zone. In the Barger process, the temperature and pressure conditions are adjusted so that the alkylation and transalkylation reactions take place in essentially the liquid phase. The transalkylation catalyst is an aluminosilicate molecular sieve including X-type, Y-type, ultrastable-Y, L-type, omega type and mordenite type zeolites with the latter being preferred. The catalyst employed in the alkylation reaction zone is a solid phosphoric acid containing material. Aluminosilicate alkylation catalysts may also be employed and water varying from 0.01 to 6 volume percent is supplied to the alkylation reaction zone. The output from the alkylation reaction zone is supplied to first and second separation zones. Water is recovered in the first separation zone. In the second separation zone, intermediate aromatic products and trialkylaromatic and heavier products are separated to provide an input to the transalkylation reaction zone having only dialkyl aromatic components, or diethylbenzene in the case of an ethylbenzene manufacturing procedure or diisopropylbenzene in the case of cumene production. A benzene substrate is also supplied to the transalkylation zone for the transalkylation reaction and the output from the transalkylation zone is recycled to the first separation zone. The alkylation and transalkylation zones may be operated in downflow, upflow, or horizontal flow configurations.

Accordingly, the art provides for various transalkylation processes to handle some of the alkylation byproducts such as diethylbenzene. It would be desirable to have a catalyst that would reduce the amount of byproducts that are not easily handled in an alkylation/transalkylation process. It is desirable to provide a catalyst that results in reduced amounts of xylene and propylbenzene in an ethylene/benzene alkylation process.

SUMMARY OF THE INVENTION

In accordance with the present invention, there is provided a process for the vapor-phase alkylation of an aromatic substrate. This is accomplished by introducing a feedstock comprising an aromatic substrate in a gaseous phase and an alkylation agent into contact with a molecular sieve aromatic alkylation catalyst to produce a reaction product containing a monoalkylated aromatic product and reduced byproducts. The catalyst is characterized in having bimodal acidity with the weak acid sites concentration of less than 50 micromoles per gram of catalyst (50 $\mu$moles/g).

The alkylation reaction may be carried out in a reaction zone having a single or a plurality of series-connected catalyst beds. The monoclinic silicalite catalysts may also be characterized by a crystal size of less than one micron, prefereably about 0.5 microns. A feedstock of an aromatic substrate, such as benzene, and an alkylating agent, such as ethylene, propylene, or alpha-olefin, is introduced into the reaction zone and the alkylation reaction zone is operated at temperature and pressure conditions in which the aromatic substrate is in a gaseous phase to cause gas-phase alkylation of the aromatic substrate in the presence of the monoclinic silicalite catalysts having bimodal acidity to produce an alkylation product. The alkylation product is then withdrawn from the reaction zone. The feedstock used may have an aromatic substrate/alkylating agent weight ratio of between about 10 to 25.

In the production of ethylbenzene or other alkylated aromatics, the alkylation product from the reaction zone may be supplied to an intermediate recovery zone for the separation and recovery of ethylbenzene from the alkylation product and for the separation and recovery of polyalkylated aromatic components. At least a portion of the polyalkylated aromatic component is supplied to a transalkylation reaction zone of the intermediate recovery zone. Benzene is supplied to the transalkylation reaction zone and the transalkylation reaction zone is operated under temperature and pressure conditions to cause disproportionation of the polyalkylated aromatic fraction to produce a disproportionation product having an enhanced ethylbenzene content and a reduced polyalkylated aromatic components content. To effect the transalkylation reaction, the transalkylation zone may contain a zeolite Y transalkylation catalyst and be operated under temperature and pressure conditions effective to maintain the feedstock in the transalkylation zone in the liquid phase.

BRIEF DESCRIPTION OF THE DRAWINGS

FIG. 1 shows the bimodal acidity of the catalysts.

FIG. 2 shows the deconvolution of the bimodal acidity curve for catalyst C.

FIG. 3 is a graph showing the xylenes formation in an ethylbenzene alkylation process in relation to the weak acid sites concentration in the catalysts.

DETAILED DESCRIPTION OF THE INVENTION

Figure 4:
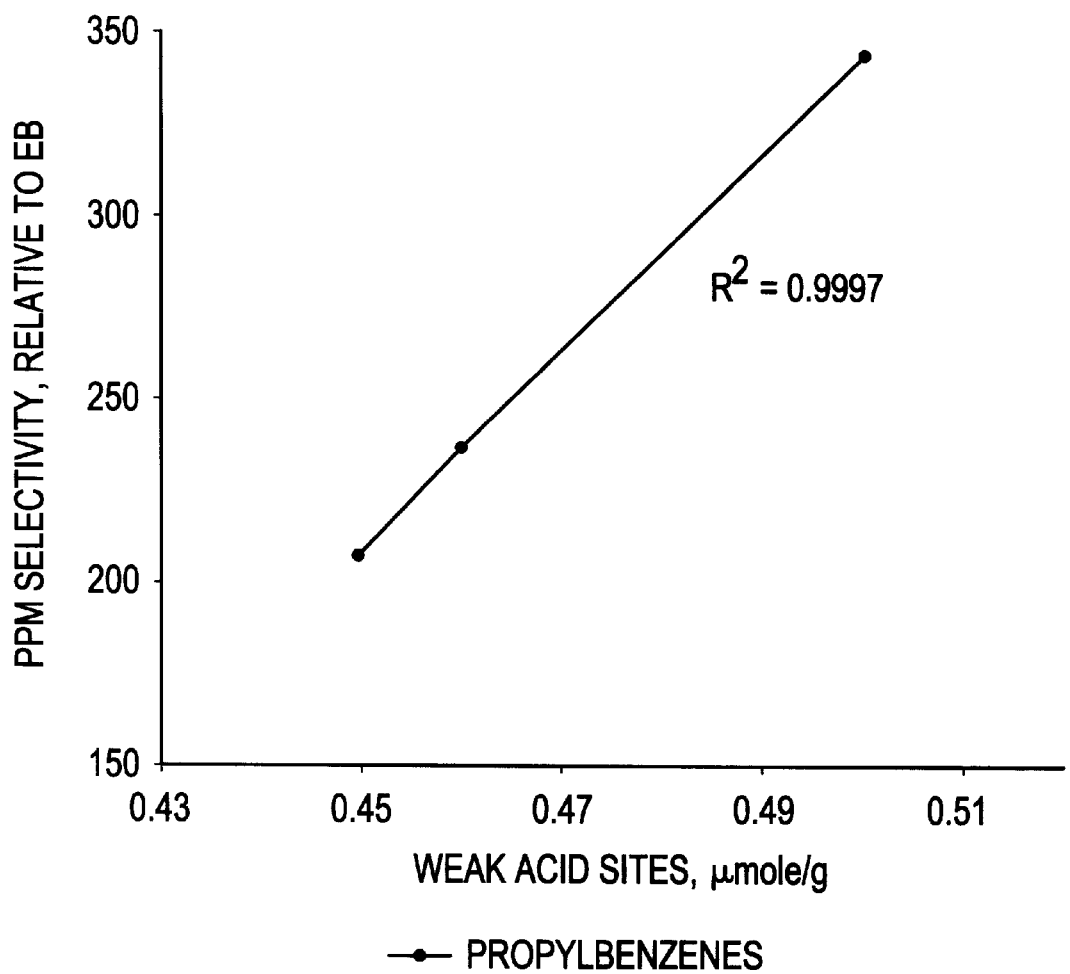
FIG. 4 is a graph showing the propylbenzene formation in an ethylbenzene alkylation process in relation to the weak acid sites concentration in the catalysts.

The present invention relates to the vapor-phase alkylation of benzene over compatible silicalite alkylation catalysts having a weak acid sites concentration of less than 50 micromoles per gram of catalyst. The process results in improved product quality and reaction efficiency. In the formation of ethylbenzene in vapor-phase alkylation from a feedstock of ethylene and benzene, other impurities and undesirable side products may be formed in addition to the desired ethylbenzene. These undesirable products include such compounds as xylene, cumene, n-propylbenzene and butylbenzene, as well as polyethylbenzenes, and high boiling point alkyl aromatic components, sometimes referred to as "heavies," having a boiling point at or above 185° C. As can be well understood, reduction of these impurities and side products is important. This is especially true in the case of xylenes. The orthoxylene (o-xylene) is a styrene contaminant that cannot be removed by distillation. The meta and para xylenes have distillation points that are in close proximity to that of ethylbenzene, or styrene and can make product separation and purification difficult. The presence of these isomers, meta and para xylenes, require high reflux and a large number of distillation stages. The propylbenzenes require additional reflux or allowing more styrene to stay in the residue, causing a decrease in yield of the desired product and an increase in residue volume. It should be pointed out that although the present invention has particular application to the formation of ethylbenzene through the alkylation of benzene with ethylene, the method may also be used to produce other alkylated aromatics, such as the formation of propylbenzene with the use of propylene as the alkylating agent. Other olefins may also be used as the alkylating agent.

Zeolite catalysts are widely used for acid-catalyzed reactions such as alkylation, cracking, isomerization, disproportionation, and so on. The number of acid sites, their strengths and accessibility, to reactant molecules, play a significant role in catalyst activity, selectivity and catalyst deactivation. It is generally accepted that only a fraction of the total number of sites is involved in a catalytic process. Often unwanted reactions occur due to the presence of acid sites of different strengths.

Three different catalyst samples were tested. The properties on these catalysts are outlined below in Table I.

TABLE I

| | Catalysts | | |
|---|---|---|---|
| Catalyst | A | B | C |
| Forms | CDS or Smooth Ext. | Same | Same |
| Size | 1/10" CDS 1/16" Smooth | Same | Same |
| Composition | Pentasil Zeolite Alumina | Pentasil Zeolite Alumina | Pentasil Zeolite Alumina |
| % LOI, 1000° F. | <5.0 wt. | <2.0 wt. | <5.0 wt. |
| Bulk Density (CBD), Lbs/ft$^3$ | CDS = 27 ± 3 Smooth = 32 ± 3 | CDS = 26.4 | CDS = 27 ± 3 |
| Surface Area, m$^2$/g min. | 275 | 275 | 225 |
| Pore Volume, cc/g > 29.2 Å | 0.50 (min.) | 0.59 | 0.48 (min.) |
| Crush Strength, Lbs/mm | >0.9 | 1.1 | >0.9 |

All catalyst samples were sized to 20–40 mesh. Approximately 0.45 grams of catalyst sample was taken in a sample tube. The thermocouple was placed at the mid-height of the catalyst bed. The sample tube was placed with TPD/TPR instrument and was tightened. The TPD (temperature programmed desorption) instrument measures the temperature required to remove ammonia from a catalyst. The higher the temperature, the stronger is the acid site. Leakage was checked by flowing an inert gas through the tube and by blocking the outlet of the vent line. If no leaks existed, blocking the end of exit line would completely stop flow of the gas. The sample temperature was raised to 650° C. at 5 degrees centigrade per minute (5° C./min) under an inert gas flow of (50 ml/min) at which temperature the catalyst was dried for 4 hours. The sample was cooled down to 100° C. The catalyst sample was saturated with ammonia (NH3) by flowing NH3 gas at 100° C. The physisorbed or weekly held NH3 was desorbed by flowing an inert gas through the sample tube (catalyst bed) at 150° C. for 2 hr. NH3 was desorbed at a temperature ramp 5° C./min to a maximum 650° C. Flow rate of sweeping gas was 50 ml/min. The experiments were repeated by changing the NH3 desorption ramp rate from 5° C./min to 10° C./min. This allowed us to see the effect of ramp rate on the peak shape and position.

Pore geometry of a catalyst, particularly zeolite catalyst, is known to control "traffic" of reactant and product molecules and thereby controls the characteristics of the products formed. The subject catalysts are silicalite based catalysts. Silicalite has an isotypic framework structure of ZSM-5 zeolite with five membered rings of Si—O or Al—O tetrahedra in the tetrahedral framework. The framework outlines a three dimensional system of intersecting channels defined by 10-rings of oxygen in all three directions with width about 6 Å in diameter. Table 2 describes the catalyst samples. These catalysts were prepared from silicalite powder and their pore size distribution was the same.

TABLE 2

Catalyst description and Na content.

| Catalyst | Na, ppm | SiO2/Al2O3 Ratio |
|---|---|---|
| A | <100 | 225 |
| B | 140 | 320 |
| C | 130 | 320 |

The acidity for each of the alkylation catalyst samples was determined by NH3-TPD after drying at 650° C. Acid sites were saturated with NH3 by flowing NH3 at 100° C. Physisorbed and weakly chemisorbed NH3 were then desorbed at 150° C. for 2 hr. Desorption at 150° C. was completed in the 2 hr as indicated by TCD signal. NH3 was then desorbed by flowing an inert gas through the catalyst bed at a ramp of 5° C./min or 10° C./min to a maximum 650° C. Unless stated otherwise acidity results obtained at desorption ramp rate 5° C./min were taken to make comparison or to examine correlation between the acidity and catalyst activity and selectivity.

TCD (thermal conductivity detector) signals (milliamp) were converted to mmole of NH3 per gram of catalyst sample as an indication of the acid sites concentration. The results are shown in Table 3. FIG. 1 shows NH3-TPD profile of the catalyst samples. All three catalyst samples showed two NH3-desorption peaks, one with peak maximum at around 240° C. and the other with peak maximum at around 350° C. These values are for the ramp rate of 5° C./min. A slight variation in the peak temperature may be attributed to a variation of the location of catalyst bed in the sample tube. The peak temperatures shown in Table 3 for the three samples were obtained by using sample weights of 0.436= 0.005 g. The number of sites reported in Table 3 were averaged from three runs and they were reproducible within 8% error. The acid sites showing peak at <300° C. and at >300° C. are classified as weak and strong acid sites. This classification is an arbitrary and relative classification and is utilized to distinguish the bimodal peaks for these catalysts. The terms should not be used to compare these catalysts with different types of catalysts of compounds. NH3-desorption peaks were separated by using the Peak-Fit deconvolution technique. The number of weak and strong acid sites was calculated from the integrated areas of peaks after peak deconvolution. As an example, the deconvoluted peaks of NH3-TPD of catalyst sample C is shown in FIG. 2. Thus the term weak acid sites is used to define the acidity attributable to the first peak of a bimodal acidity curve. This is the peak at the lower temperature values in a bimodal acidity curve as shown in FIGS. 1 and 2.

An increased desorption ramp rate (10° C./min) shifted peak maxima to higher temperatures. The number of total acid sites was found to be in an excellent agreement (±0.001 mmole/g).

Catalysts B and C were shown to possess decreased amounts of total acid sites compared to that of catalyst A.

The smaller amounts of acid sites of catalysts B and C are attributed to lower aluminum contents (or higher $SiO_2/Al_2O_3$ ratio) of the silicalite powders used for making these catalysts. In addition, catalysts B and C powder samples have slightly higher sodium (Na) contents than catalyst A. Sodium ions are known to reduce zeolite acidity. It is important to note that the three catalyst samples show a smaller variation in weak acid sites compared to strong acid sites. The results suggest the decrease of framework aluminum attributes to preferential reduction of strong acid sites with less of an effect on the weak acid sites.

TABLE 3

Acidity of catalysts determined by NH3-TPD.

| Catalyst | Weak (Tmax, °C.) | Strong (Tmax, °C.) | Total | NH3-Des Ramp Rate |
|---|---|---|---|---|
| A | 0.050 (237) | 0.143 (356) | 0.193 | 5° C./min |
|   | 0.045 (252) | 0.149 (377) | 0.194 | 10° C./min |
| B | 0.046 (235) | 0.109 (346) | 0.155 | 5° C./min |
|   | 0.040 (251) | 0.113 (365) | 0.153 | 10° C./min |
| C | 0.045 (241) | 0.119 (351) | 0.158 | 5° C./min |
|   | 0.032 (245) | 0.124 (347) | 0.156 | 10° C./min |

Table 4 summarizes some of the byproducts formation for each of the tested catalysts for benzene alkylation with ethylene at gas phase conditions (single pass, Tinlet=400° C., LHSV 70 hr-1). Product selectivities to total xylenes, propylbenzenes, butylbenzenes and heavies are given in Table 4. FIGS. 3 and 4 show plots of catalyst selectivities to xylenes, and propylbenzenes as a function of catalyst weak acid sites. Linear lines were drawn and $R^2$ values are shown in Table 5.

As indicated earlier, the three catalyst samples showed a smaller difference in number of weak acid sites. However, a small increase of the weak acid sites was found to increase the formation of xylenes and propylbenzenes.

TABLE 4

Catalyst deactivation and by-product selectivity of benzene alkylation.[a]

| | PPM Selectivity, Relative to EB | | |
|---|---|---|---|
| Catalyst | Xylenes | PropylBZ | ButylBZ |
| A | 85 | 345 | 335 |
| B | 56 | 237 | 322 |
| C | 48 | 207 | 266 |

TABLE 5

$R^2$-Values

| | $R^2$ | | |
|---|---|---|---|
| | Weak Acid Sites | Strong Acid Sites | Correlation exists with |
| Xylene | 0.9997 | 0.7726 | Weak acid sites |
| PropylBZ | 0.9997 | 0.7715 | Weak acid sites |
| ButylBZ | 0.6057 | 0.1601 | No good correlation |

In one embodiment of the present invention, a multi-stage alkylation reactor having a plurality of alkylation catalyst beds in series is employed. One or more of the catalyst beds contain the silicalite alkylation catalyst of the present invention having a weak acid site concentration of less than fifty micromoles per gram (<50 μmoles/g). Preferably, the catalyst of the present invention has a weak acid site concentration of less than 48 μmoles/g. While the catalyst of the present invention can be utilized alone, it is also contemplated that one or more of the catalyst beds contain other alkylation catalysts. The combination of catalysts is utilized to optimize the catalyst life and yield.

Silicalite, as is well known in the art, is a molecular sieve catalyst which is similar to the ZSM-5 zeolites but is typically characterized by a higher silica/alumina ratio providing an aluminum/unit cell ratio of less than 1, and in addition, is normally characterized as having a somewhat larger than average crystal size than is commonly associated with the ZSM zeolites. As is well known in the art, silicalite, which in the as-synthesized form is characterized by orthorhombic symmetry, can be converted to monoclinic symmetry by a calcination procedure as disclosed, for example, in U.S. Pat. No. 4,599,473 to DeBras et al. As described in detail in DeBras et al., "Physico-chemical characterization of pentasil type materials, I. Precursors and calcined zeolites, and II. Thermal analysis of the precursors," *Zeolites*, 1985, Vol. 5, pp. 369–383, the silicalite typically has a relatively large crystal size. Thus, at an average of less than one aluminum atom per unit cell (a silica/alumina ratio of about 200) silicalite typically has an average crystal size of perhaps 5–10 microns or more. The aforementioned U.S. Pat. No. 4,489,214 to Butler et al. discloses experimental work involving the ethylation of toluene over silicalite of a crystal size greater than one micron, ranging from 1–2 microns up to 8 microns. The silicalite is further characterized in terms of a variable aluminum gradient such that the aluminum gradient is positive when going from the interior to the surface of the molecular sieve crystal. That is, the silicalite can be characterized by a core portion which is relatively aluminum deficient with an outer shell portion which is relatively aluminum rich. It is to be understood that the term "aluminum rich" is a relative term and that for silicalite even the outer shell portion of the crystallite has a low aluminum content.

In another embodiment, vapor-phase alkylation using silicalite catalyst as described herein is followed by a liquid phase transalkylation procedure in which the alkylation and transalkylation reactors are integrated with an intermediate recovery zone, preferably involving a plurality of separation zones operated in a manner to effectively provide feed streams to the reactors with recycle of the output from the transalkylation reactor to a benzene recovery zone downstream of the alkylation reactor. In this integrated mode of operation, the transalkylation product is applied to an initial stage of a benzene recovery zone. Subsequent separation steps are carried out in a manner to apply a split feed to the transalkylation reactor. The preferred catalyst used in the transalkylation reactor is a molecular sieve having a pore size greater than the pore size of the silicalite catalyst. Preferably, the transalkylation catalyst is zeolite Y. The alkylation reactor is preferably operated at substantially higher temperature conditions than the transalkylation reactor. In one embodiment of the invention, the recycled output from the transalkylation reactor is passed in a heat exchange relationship with the alkylation reactor product feed to the initial separation zone.

Preferably, the alkylation reactor comprises at least four catalyst beds as described above. More beds can be provided, and it will sometimes be advantageous to provide at least five or six catalyst beds in the alkylation reactor. The reactor is operated so as to provide vapor phase alkylation (both the aromatic substrate and the alkylating agent are in the vapor phase) at temperatures ranging from about 630° F.–800° F. at the inlet to about 700° F.–850° F. at the outlet. The pressure may be within the range of about 250 to 450 psia with the pressure decreasing from one bed to the next as the temperature increases. By way of example, the benzene and ethylene supplied to the top of the reactor may enter the reactor at a temperature of about 740° F. and a pressure of about 430 psia. The alkylation reaction is exothermic so that the temperature progressively increases from the first to the last catalyst bed by way of example. The interstage temperatures may increase from 750° F. for the first catalyst bed to 765° F. after the second catalyst bed to 820° F. after the third catalyst bed to a temperature of about 840° F. after the last catalyst bed.

Normally in the operation of multi-stage reaction zone, a benzene-ethylene mixture is introduced to the first catalyst bed at the initial stage of the reaction zone and also in between the several successive stages of catalyst beds. In the examples presented, ethylene is supplied along with benzene to the first catalyst bed located at the top or upper end of the reactor. In addition, interstage injection of ethylene and benzene is provided for between the subsequent catalyst beds. The feedstock benzene-to-ethylene weight ratio injected into the top of the alkylation reactor may be between about 18 to 22.

The silicalite alkylation catalysts, as referred to herein, are molecular sieves from the pentasil family of high silica molecular sieves. Such pentasil molecular sieves are described, for example, in Kokotailo et al., "Pentasil Family of High Silica Crystalline Materials," Chem. Soc. Special Publ. 33, 133–139 (1980). The silicalite molecular sieve alkylation catalysts have a somewhat smaller pore size than the preferred zeolite-Y employed in the transalkylation reactor. The silicalite crystals have an effective pore size or window within the range of 5–6 angstroms. Zeolite Y has a pore size of about 7 angstroms.

Preferred silicalites for the catalysts used in the present invention are extruded with an alumina binder in a "trilobe" shape having a nominal diameter of about 1/16" and a length of the extrudate of about 1/6–1/4." The "trilobe" cross sectional shape is something on the order of a three leaf clover. The purpose of this shape is to increase the surface area of the extruded catalyst beyond what one would expect with a normal cylindrical extrudate. The silicalite catalysts used are characterized as monoclinic silicalite. Monoclinic silicalite may be prepared as disclosed in U.S. Pat. No. 4,781,906 to Cahen et al. and U.S. Pat. No. 4,772,456 to DeClippeleir et al. The silicalite catalyst typically contains small amounts of sodium and iron.

As noted previously, the silicalite alkylation catalysts have a crystal structure characterized by an aluminum rich outer shell and an aluminum deficient interior portion when compared with the outer shell. The silicalite catalysts are dry and have no appreciable or intended water content. Specifically, the silicalite catalysts preferably contain no more than about 200 ppm sodium, preferably no more than about 100 ppm sodium, and no more than about 500 ppm iron, preferably no more than about 300 ppm iron. The alumina binder is a high purity alumina such as "catapal alumina." Preferably, the alumina binder is characterized in terms of an unusually high pore size and unusually low sodium content. As noted previously, the silicalite itself has a low sodium content in its crystalline structure. By maintaining a low sodium content in the alumina, a high portion of the catalyst sites in the silicalite structure are maintained in the active hydrogen form—that is, the low sodium content of the binder tends to minimize neutralization of the crystalline catalyst sites due to ion exchange between sodium in the binder and the acid sites in the catalyst. The alumina binder is further characterized in terms of a relatively large average pore size after the catalyst is extruded and divided into particles. Specifically, the average pore size of the binder, which can be termed the "maximum" pore size to avoid confusion with the pore size of the silicalite itself, is about 1,000 angstroms or more, preferably within the range of 1000 to 4000 angstroms. A preferred pore size range is within the range of about 1,000 to about 1,800 angstroms. This relatively large pore size binder can enhance the efficiency of the catalyst by avoiding, or at least minimizing, an alumina-diffusing mechanism as applied to the catalyst particles themselves, thus enhancing access to the silicalite molecular sieve within the catalyst particles. The pore size of the molecular sieve structure itself normally can be expected to be on the order of about 5–6 angstroms. The silicalite catalysts preferably contain only a small amount of sodium, about 70–200 ppm sodium, and contain only a small amount of iron, about 200–500 ppm. The catalyst need not contain any additional "promoter" metals incorporated during the synthesis of the catalyst.

Having described specific embodiments of the present invention, it will be understood that modifications thereof may be suggested to those skilled in the art, and it is intended to cover all such modifications as fall within the scope of the appended claims.

What is claimed is:

1. A method for the vapor-phase alkylation of an aromatic substrate comprising:

providing an alkylation reaction zone having at least one catalyst bed containing a monoclinic silicalite catalyst having a weak acid site concentration of less than 50 micromoles per gram; and at least one other catalyst bed containing a second monoclinic silicalite catalyst, introducing feedstock of an aromatic substrate and an alkylating agent into the reaction zone;

operating the alkylation reaction zone at temperature and pressure conditions in which the aromatic substrate is in a gaseous phase to cause gas-phase alkylation of the aromatic substrate in the presence of the monoclinic silicalite catalysts to produce an alkylation product; and withdrawing the alkylation product from the reaction zone.

2. The method of claim 1, wherein:

the aromatic substrate is benzene and the alkylating agent is an ethylating or propylating agent.

3. The method of claim 1, wherein:

the feedstock has an aromatic substrate/alkylating agent weight ratio within the range of about 10 to 25.

4. The method of claim 1, wherein:

the catalyst has a weak acid site concentration of less than 48 micromoles per gram.

5. The method of claim 1, wherein:

the alkylation agent is an alpha-olefin.

6. A method for the vapor-phase ethylation of benzene comprising:

providing an alkylation reaction zone having at least one catalyst bed containing a monoclinic silicalite catalyst having a weak acid site concentration of less than 50 micromoles per gram;

introducing a feedstock of benzene and ethylene into the reaction zone;

operating the alkylation reaction zone at temperature and pressure conditions in which the benzene is in a gaseous phase to cause gas-phase ethylation of the benzene to produce an alkylation product comprising ethylbenzene; and withdrawing the alkylation product from the reaction zone and separating and recovering ethylbenzene from the alkylation product.

7. The method of claim 6, wherein:

the alkylation product from the reaction zone comprises reduced levels of xylenes as compared to similar reactions carried out with monoclinic silicalite catalysts having a higher concentration of weak acid sites.

8. The method of claim 6, wherein:

the alkylation product from the reaction zone comprises reduced levels of propylbenzene as compared to similar reactions carried out with monoclinic silicalite catalysts having a higher concentration of weak acid sites.

9. The method of claim 6, wherein:

the alkylation product from the reaction zone comprises reduced levels of butylbenzene as compared to similar reactions carried out with monoclinic silicalite catalysts having a higher concentration of weak acid sites.

10. The method of claim 6, wherein:

the feedstock has a benzene/ethylene weight ratio within the range of about 10 to 25.

11. The method of claim 6, wherein:

the reaction zone comprises between 4 to 8 catalyst beds.

12. The method of claim 1, wherein the monoclinic silicalite catalyst, having a weak acid site concentration, is further characterized by having bimodal acidity, designated as weak acid sites and strong acid sites.

13. The method of claim 6, wherein the monoclinic silicalite catalyst, having a weak acid site concentration, is further characterized by having bimodal acidity, designated as weak acid sites and strong acid sites.

* * * * *